United States Patent [19]

Ruoslahti et al.

[11] Patent Number: 5,627,263
[45] Date of Patent: May 6, 1997

[54] INTEGRIN-BINDING PEPTIDES

[75] Inventors: Erkki Ruoslahti, Rancho Santa Fe; Erkki Koivunen, San Diego, both of Calif.

[73] Assignee: La Jolla Cancer Research Foundation, La Jolla, Calif.

[21] Appl. No.: 425,238

[22] Filed: Apr. 18, 1995

Related U.S. Application Data

[63] Continuation of Ser. No. 158,001, Nov. 24, 1993, abandoned.
[51] Int. Cl.⁶ .............................. A61K 38/04; C07K 7/06; C07K 7/08
[52] U.S. Cl. ............................................. 530/327; 530/328
[58] Field of Search ................................. 530/327, 328, 530/329; 514/14, 15, 16

[56] References Cited

PUBLICATIONS

Koivunen et al., "Phage Libraries Displaying Cyclic Peptides with Different Ring Sizes: Ligand Specificities of the RGD–Directed Integrins," *Bio/Technology* 13:265–270 (1995).
Yamada, Kenneth M., "Adhesive Recognition Sequences," *J. Biol. Chem.* 266:12809–12812 (1991).
O'Neil et al., "Identification of Novel Peptide Antagonists for GPIIb/IIIa from a Conformationally Constrained Phage Peptide Library," *Proteins* 14:509–515 (1992).
Koivunen, Erkki et al., "Isolation of a Highly Specific Ligand for the $\beta_5\beta_1$ Integrin from a Phage Display Library." *J. Cell Biol.* 124:373–380 (1994).
Koivunen, Erkki et al., "Selection of Peptides Binding to the $\alpha_5\beta_1$ Integrin from Phage Display Library." *J. Biol. Chem.* 268:20205–20210 (1993).
Peishoff, Catherine, E. et al., "Investigation of Conformational Specificity at GPIIb/IIIa: Evaluation of Conformationally Constrained RGD Peptides." *J. Med. Chem.* 35:3962–3969 (1992).
Samanen, J. et al., "Development of a Small RGD Peptide Fibrinogen Receptor Antagonists with Potent Antiaggregatory Activity in Vitro." *J. Med. Chem.* 34:3114–3125 (1991).
Skubitz, Amy P.N. et al., "Synthetic Peptides from the Carboxy–terminal Globular Domain of the A Chain of Laminin: Their Ability to Promote Cell Adhesion and Neurite Ourgrowth, and Interact with Heparin and the β1 Integrin Subunit." *J. Cell. Biol.* 115:1137–1148 (1991).

Pierschbacher, Michael D. and Ruoslahti, Erkki "Cell Attachment Activity of Fibronectin Can Be Duplicated by Small Synthetic Fragments of the Molecule." *Nature.* 309:30–33 (1984).
Pytela, Robert et al. "Identification and Isolation of a 140 kd Cell Surface Glycoprotein with Properties Expected of a Fibronectin Receptor." *Cell.* 40:191–198 (1985).
Pytela, Robert et al. "A 125/115–kDa Cell Surface Receptor Specific for Vitronectin Interacts with the Arginine–Glycine–Asparic Acid Adhesion Sequence Derived for Fibronectin." *Proc. Natl. Acad. Sci. USA.* 82:5766–5770 (1985).
Pierschbacher, Michael D. and Ruoslahti, Erkki, "Influence of Sterochemistry of the Sequence Arg–Gly–Asp–Xaa on Binding Specificity in Cell Adhesion." *J. Biol. Chem.* 262:17294–17298 (1987).
Pytela, Robert et al, "Arginine–Glycerine–Aspartic Acid Adhesion Receptors." *Method in Enzy.* 144:475–489 (1987).
Yamada, Kenneth M. and Kennedy, Dorothy W. "Peptide Inhibitors of Fibronectin, Laminin, and Other Adhesion Molecules: Unique and Shared Features." *J. Cell. Physilolgy* 130:21–28 (1987).
Gurrath, Marion et al. "Conformation/Activity Studies of Rationally Designed Potent Anti–adhesive RGD Peptides." *Eur. J. Biochem.* 210:911–921 (1992).
Rudinger, J. (1976). Peptide Hormones, University Park Press, Baltimore.
Koivunen et al., *J. Cell Biol.* vol. 124 No. 3 pp. 373–380 (1994).
Koivunen et al., *J. Biol. Chem.* vol. 268 No. 27 pp. 20205–20210, (1993).
Argraves et al., *J. Cell Biol.* vol. 105, Sep. 1987 pp. 1183–1190.

*Primary Examiner*—Elizabeth C. Weimar
*Assistant Examiner*—Anish Gupta
*Attorney, Agent, or Firm*—Campbell & Flores LLP

[57] ABSTRACT

The present invention provides peptides having specificity for fibronectin-binding and vitronectin-binding integrins, and in particular for $\alpha_5\beta_1$ integrin. These peptides are characterized by having the ability to interfere with fibronectin binding to $\alpha_5\beta_1$ integrin, to block attachment of cells expressing integrins to extracellular matrix proteins and to promote cell attachment when immobilized onto a surface.

2 Claims, 4 Drawing Sheets

FIG. 8

INTEGRIN-BINDING PEPTIDES

This invention was made with government support under grants CA42507, CA28896 and Cancer Center Support Grant CA30199 awarded by the National Institutes of Health. The government has certain rights to this invention.

This application is a continuation of application Ser. No. 08/158,001, filed Nov. 24, 1993 now abandoned.

BACKGROUND OF THE INVENTION

Integrins are transmembrane $\alpha\beta$ heterodimer receptors that are expressed on a wide variety of cells and are involved in extracellular matrix interactions. There are eight known $\beta$ subunits and fourteen known $\alpha$ subunits, which associate in various combinations to form at least twenty receptors with different ligand specificities. The ligands for several of the integrins are adhesive extracellular matrix (ECM) proteins such as fibronectin, vitronectin, collagens and laminin.

It is becoming increasingly clear that the ECM influences gene expression and that changes in the expression of genes encoding matrix proteins alter the composition of the ECM. Integrins appear to mediate "messages" from the exterior of a cell to its interior, thereby inducing changes in gene expression. In this capacity, the integrins control many medically important biological phenomena, including cell migration during development, tissue repair, cancer cell differentiation, metastasis of tumor cells, platelet aggregation and homing of immune system cells and neuronal processes to target sites.

Many integrins, including $\alpha_5\beta_1$, recognize the amino acid sequence RGD (arginine-glycine-aspartic acid), which is present in fibronectin and other adhesive proteins to which the integrins bind. Peptides and protein fragments containing the RGD sequence can be used to modulate the activity of the RGD-recognizing integrins.

Fibronectin is the only known protein ligand for the $\alpha_5\beta_1$ integrin and the binding of fibronectin to this integrin is mediated by an RGD sequence. In contrast, the integrins, $\alpha_v\beta_3$ and $\alpha_{IIb}\beta_3$, which also recognize the RGD sequence, can bind many different adhesive proteins.

The $\alpha_5\beta_3$ integrin is important in promoting the assembly of fibronectin matrix and initiating cell attachment to fibronectin. The $\alpha_5\beta_1$ integrin also appears to have a crucial role in mediating the migration of cells. The use of ligands that are specific for the $\alpha_5\beta_1$ integrin receptor may permit modulation and manipulation of cell migration in various medical situations, including during wound healing, tissue repair and tumor invasion. Thus, a need exists to develop drug-like ligands that selectively bind with high affinity to an individual integrin. The present invention satisfies this need and provides related advantages as well.

SUMMARY OF THE INVENTION

The present invention provides peptides that are recognized by and selectively bind to the $\alpha_5\beta_1$ integrin. The peptides of the present invention are characterized by their ability to interfere with fibronectin binding to $\alpha_5\beta_1$ integrin and to block integrin-mediated cell attachment to extracellular matrix proteins. When immobilized onto a surface, these peptides can promote cell attachment through integrin binding.

DETAILED DESCRIPTION OF THE INVENTION

The present invention provides peptides that are recognized by and bind to the $\alpha_5\beta_1$ integrin.

Embodiments of the present invention include the peptide motifs, RRETAWA [SEQ ID NO:5] and CRRETAWAC [SEQ ID NO:6]. In particular, the cyclic CRRETAWAC [SEQ ID NO:6] is a novel structure that is characterized by having a high binding affinity for $\alpha_5\beta_1$ integrin.

The peptides of the present invention can be synthesized using well known methods including methods of recombinant DNA technology and chemical synthesis. A linear peptide can be synthesized, for example, by the solid phase peptide synthesis method of Merrifield using an automated peptide synthesizer (*J. Am. Chem. Soc.*, 85:2149 (1964), which is incorporated herein by reference). Alternatively, a peptide of the present invention can be synthesized using standard solution methods well known in the art (see, for example, Bodanszky, M., *Principles of Peptide Synthesis* (Springer-Verlag, 1984), which is incorporated herein by reference). Such newly synthesized peptides can be obtained in relatively pure form using, for example, high performance liquid chromatography (HPLC) and can be characterized using, for example, mass spectrometry or amino acid sequence analysis. Although a purity of greater than 95 percent for the synthesized peptide is preferred, lower purity may be acceptable.

The peptides of the present invention are particularly useful when they are maintained in a constrained secondary conformation. As used herein, the terms "constrained secondary structure," "stabilized" and "conformationally stabilized" indicate that the peptide bonds comprising the peptide are not able to rotate freely in space but, instead, are maintained in a relatively fixed structure. It is well known that a peptide having a constrained secondary structure is more likely to be selectively bound by a specific receptor.

Various methods for constraining the secondary structure of a peptide are well known in the art. For example, a peptide such as RRETAWA [SEQ ID NO:5] and CRRETAWAC [SEQ ID NO:6] can be stabilized into a constrained secondary structure by incorporating the peptide into a larger peptide sequence that forms a known secondary structure. For example, a peptide of the present invention can be stabilized by incorporating it into a sequence that forms a helix such as an alpha (α) helix or a triple helix, according to methods described, for example, by Dedhar et al., *J. Cell Biol.* 104:585 (1987); by Rhodes et al., *Biochemistry* 17:3442 (1978); and by Carbone et al., *J. Immunol.* 138:1838 (1987), each of which is incorporated herein by reference.

A particularly useful way for constraining the secondary structure of a newly synthesized linear peptide is to cyclize the peptide using any of various methods well known in the art. For example, a cyclized peptide of the present invention can be prepared by forming a peptide bond between non-adjacent amino acid residues as described, for example, by Schiller et al., *Int. J. Pept. Prot. Res.* 25:171(1985), which is incorporated herein by reference. Peptides can by synthesized on the Merrifield resin by assembling the linear peptide chain using $N^\alpha$-Fmoc-amino acids and Boc and tertiary-butyl protein, then, following release of the peptide from the resin, a peptide bond can be formed between the amino and carboxy termini.

A newly synthesized linear peptide also can be cyclized by the formation of a bond between reactive amino acid side chains. For example, a peptide containing a cysteine-pair can be synthesized and a disulfide bridge can be formed by oxidizing a dilute aqueous solution of the peptide with $K_3[F_e(CN)_6]$. Alternatively, a lactam such as an ε(γ-glutamyl)-lysine bond can be formed between lysine and glutamic acid residues, a lysinonorleucine bond can be formed between lysine and leucine residues or a dityrosine bond can be formed between two tyrosine residues. Cyclic peptides can also be constructed to contain, for example, four lysine residues, which can form the heterocyclic structure of desmosine (see, for example, Devlin, Textbook of Biochemistry 3d ed. (1992), which is incorporated herein by reference). Methods for forming these and other bonds are well known in the art and are based on well known rules of chemical reactivity (Morrison and Boyd, Organic Chemistry 6th ed. (Prentice Hall 1992), which is incorporated herein by reference).

As used herein, the term "amino acid" and any reference to a specific amino acid is generally meant to include naturally occurring proteogenic amino acids as well as non-naturally occurring amino acids such as amino acid analogs. In view of this broad definition, one skilled in the art would know that reference herein to an amino acid, unless specifically indicated otherwise, includes, for example, naturally occurring proteogenic (L)-amino acids, (D)-amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well known metabolic pathways.

The choice of including an (L)- or a (D)-amino acid in a peptide of the present invention depends, in part, on the desired characteristics of the peptide. For example, the incorporation of one or more (D)-amino acids can confer increased stability on the peptide in vitro or in vivo. The incorporation of one or more (D)-amino acids also can increase or decrease the binding activity of the peptide as determined, for example, using the binding assays described herein, or other methods well known in the art. In some cases, such as when treating a subject, it may be desirable to allow the peptide of the invention to remain active for only a short period of time. In those cases, the incorporation of one or more (L)-amino acids in the peptide can allow, for example, endogenous peptidases in the subject to digest the peptide in vivo, thereby limiting the subject's exposure to an active peptide.

As used herein, the term "amino acid equivalent" refers to compounds which depart from the structure of the naturally occurring amino acids, but which have substantially the structure of an amino acid, such that they can be substituted within a peptide which retains its biological activity. Thus, for example, amino acid equivalents can include amino acids as described above, which have side chain modifications or substitutions or which belong to a related class of organic acids such as amides or the like. The term "amino acid," as described above, is intended to include amino acid equivalents. The term "residues" also can refer to an amino acid or an amino acid equivalent and is synonymous with these terms.

As used herein, the term "peptide" is used in its broadest sense to refer to compounds containing two or more amino acids, which include amino acid equivalents and other non-amino acid groups, that retain the desired functional activity characteristic of a peptide of the present invention. Peptide equivalents can differ from conventional peptides by the replacement of one or more amino acids with related organic acids (such as PABA), amino acids or the like or the substitution or modification of side chains or functional groups.

As used herein, the term "binding" refers to the ability of an integrin-coated surface to interact with a peptide, for example, such that the interaction between the integrin and the peptide is relatively specific. A used herein, the term "relatively specific" means that the affinity of binding of an integrin and a peptide of the present invention is about $1 \times 10^{-5}$M or less. Thus, the definition of the term "binding" is limited to exclude nonspecific binding, which can occur for various reasons such as non-specific adsorption to a surface. Non-specific binding can be readily identified by including the appropriate controls in a binding assay. Methods for determining the affinity of an integrin with a peptide of the present invention are well known and described in the examples, below.

A distinctive characteristic of such binding is that the bound peptide can be detached or prevented from binding to an integrin by specific elution or initial contact, respectively, with the fibronectin-derived synthetic GRGDSP peptide (see Pytela et al. Cell 40: 191–198 (1985); Pytela et al. *Proc. Natl. Acad. Sci., USA* 82:5766–5770 (1985), each of which is incorporated herein by reference). In addition, specific binding can be disrupted using an agent such as EDTA, which renders an integrin inactive, or using a nonspecific protein denaturant such as low pH buffer, as described in the procedures set-out below.

Using the binding assays described herein and other binding assays well known in the art, the relative binding affinity of a peptide of the invention for an integrin can be determined. As used herein, the term "relative binding affinity" refers to the ability of one peptide, as compared to a second peptide, to inhibit the binding to an integrin of an RGD peptide such as GRGDSP (see Examples VI and VII). The relative binding affinity of a peptide is determined by competitive binding assays which identify peptide motifs that can inhibit the binding of a peptide to an integrin. The relative binding affinity of various peptides of the invention can be compared by determining the half-maximal inhibitory concentration ($IC_{50}$) of these peptides. Typically, the peptides of the invention are compared with a standard integrin-binding peptide such as the fibronectin-derived peptide, GRGDSP [SEQ ID NO:7].

As used herein the term "high binding affinity" refers to peptides that have an $IC_{50}$ of $1\times10^{-7}M$ or less in a competitive binding assay for integrin (see Examples VI and VII). The term "high binding affinity" also can refer to a peptide that is expressed on a phage. Peptides having a high binding affinity are characterized by the ability to bind integrins immobilized on a surface at very low concentration such as about 10 ng/well.

As used herein the terms "selective binding" or "selectively binds" refers to a peptide that has a binding affinity only or predominately for the designated integrin. Selective binding can be determined by identifying, for example, the peptide's ability to inhibit binding of an RGD-containing peptide to a particular integrin such as the $\alpha_5\beta_1$ integrin but not to other integrins.

It is to be understood that limited modifications can be made to a peptide without destroying its biological function. Thus, modification of the peptides of the present invention that do not completely destroy its activity are within the definition of the compound claims as such. Modifications can include, for example, additions, deletions or substitutions of amino acid residues, substitutions with compounds that mimic amino acid structure or functions as well as the addition of chemical moieties such a amino and acetyl groups. The modifications can be deliberate or accidental, and be modifications of the composition or the structure.

The cyclic peptide GA*CRRETAWAC*GA [SEQ ID NO:3], herein referred to as RRETAWA [SEQ ID NO:5] or CRRETAWAC [SEQ ID NO:6], was synthesized and its activity was compared to the cyclic RGD-containing peptide GA*CRGDC*LGA. The "*" indicates the cysteine residues involved in forming the disulfide bridge.

Conformationally constrained peptides have an increased affinity for integrins. The importance of the cyclic structure formed by the disulfide bond in the peptide sequences isolated as described herein is indicated by the fact that the binding activity of the RRETAWA peptide was significantly decreased following reduction of the disulfide bond and alkylation of the cysteine residues.

The identification of a RRETAWA [SEQ ID NO:5] sequence as a motif that specifically bound to an integrin was surprising in that the RRETAWA [SEQ ID NO:5] motif bears no obvious similarity to the portion of the fibronectin sequence, or other ligand sequences, known to bind $\alpha_5\beta_1$ or other integrins. Because of its divergent sequence, we determined whether RRETAWA [SEQ ID NO:5] interacted with a site in $\alpha_5\beta_1$ other than the RGD binding site. Three different assays, including a fibronectin-binding assay, cell attachment to fibronectin and cell attachment to the RRETAWA [SEQ ID NO:5] peptide, indicated that RRETAWA and RGD compete with each other in the binding to $\alpha_5\beta_1$ (see Example V). Moreover, the binding of cells to immobilized RRETAWA [SEQ ID NO:5] peptide was inhibited by EDTA, indicating that the interaction is divalent cation-dependent.

The results of these experiments indicate that RRETAWA [SEQ ID NO:5] binds to an integrin at the same site as RGD or in a site that is in direct connection with the RGD-binding pocket in $\alpha_5\beta_1$ integrin. The RRETAWA [SEQ ID NO:5] peptide has two positive charges and one negative charge, which are likely to play a role in its binding to an integrin.

Figure 1:
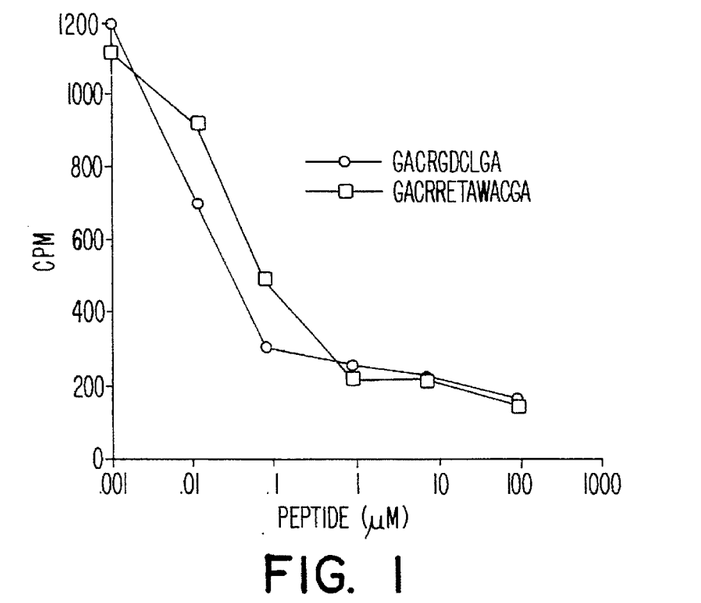
FIG. 1 shows the inhibition of $^{125}$I-fibronectin binding to $\alpha_5\beta_1$ integrin by synthetic cyclic peptides.

Because of their ability to bind to integrins, the peptides of the present invention can be used to prevent integrin-expressing cells such as tumor cells from binding to fibronectin by administering an effective amount of the appropriate peptide to the cells. An effective amount of a peptide can be determined using the methods described herein. For example, as shown in FIG. 1, an effective amount of the claimed peptide can be determined using an assay to identify the inhibition of fibronectin adhesion. Since fibronectin adhesion has a role in the process of metastasis, experiments such as those described in FIG. 1 can provide information as to an effective amount of a peptide for inhibiting fibronectin adhesion and, therefore, metastasis.

The peptides of the present invention also can be useful to promote attachment of integrin-expressing cells to a surface by coating the surface with the peptides. The peptides of the present invention are particularly useful because they are readily and inexpensively synthesized and, therefore, are more readily available, for example, than antibodies specific for an integrin or integrin subunits. For example, the peptides can be administered to the site of a wound, thus mediating the binding of integrin-expressing cells and increasing the rate of wound healing.

The invention provides pharmaceutical compositions comprising a peptide of the present invention and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the peptide of the present invention or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the integrin-binding peptide and on the particular physicochemical characteristics of the specific peptide.

The invention further relates to methods of administering a pharmaceutical composition comprising a peptide of the present invention to a subject in order, for example, to promote wound healing in the subject or to prevent the spread and infiltration of metastatic tumor cells. One skilled in the art would know that a pharmaceutical composition comprising a peptide of the present invention can be administered to a subject having a wound or a cancer that is likely to metastasize by various routes, depending on the specific pathologic condition. For example, where the treatment is localized such as for inducing healing of a wound, a pharmaceutical composition comprising a peptide of the present invention can be suspended or dissolved in the appropriate pharmaceutically acceptable carrier and administered topically. Alternatively, where treatment is systemic due, for example, to the presence in the subject of metastatic tumor cells, the composition can be administered orally or parenterally, such as intravenously, intramuscularly, subcutaneously, intraorbitally, intracapsularly, intraperitoneally or intracisternally.

The total effective amount of a peptide of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a peptide of the present invention required to obtain an effective dose in a subject depends on many factors including the age and general health of the subject as well as the route of administration and the number of treatments to be administered. In view of these factors, the skilled artisan would adjust the dose so as to provide an effective dose for a particular use.

The peptides of the present invention, including those peptides specific for $\alpha_5\beta_1$ integrin, also can be used for identifying and isolating cell types that express particular integrins. For example, cells that express the $\alpha_5\beta_1$ integrin can be identified and isolated from a tissue by coating a surface or column with the RRETAWA [SEQ ID NO:5] peptide, which has specificity for the $\alpha_5\beta_1$ integrin, allowing the cells to bind to the surface or column and eluting the bound cells from the surface or column using, for example, the same peptide or EDTA-containing buffer. This method may be particularly useful for isolating lymphocyte subpopulations that express various integrins. Such peptide columns also can be used to purify integrins, (see Pytela et al., *Meth. Enzymol.* 82:803-831 (1987), which is incorporated herein by reference).

The invention will now be described in greater detail by reference to the following examples. These examples are intended to illustrate but not limit the invention.

EXAMPLE I

FIBRONECTIN BINDING ASSAY

Polyclonal antibodies against the cytoplasmic tails of $\alpha_5$, $\alpha_v$ and $\beta_3$ subunits were prepared by immunizing rabbits with the synthetic peptides described below according to the methods described by Freed et al., *EMBO J* 8:2955-2965 (1989); by Giancotti et al., *Cell* 60:849-859 (1990); and by Vogel et al., *J. Cell. Biol.* 121:461-468 (1993). The immunizing peptides were used to affinity purify the antibodies using methods well known in the art (Harlow et al., *Antibodies: A Laboratory Manual*, Cold Spring Harbor (1989), which is incorporated herein by reference).

The $\alpha_5\beta_1$ integrin was bound to $\alpha_5$ specific antibody-coated wells by incubating 300 µl of a placental extract per well in TBS buffer containing 0.1M octylglucoside, 1 mM CaCl$_2$, 1 mM MnCl$_2$ and proteinase inhibitors overnight at 4° C., as described by Pytela et al. (1987), supra. Alternatively, the $\alpha_5\beta_1$ integrin was directly coated on plastic as described above. The wells were extensively washed with TBS containing 0.1% NP-40. $^{125}$I-labeled fibronectin (100,000 cpm per well) was incubated in the presence of competing peptides for 1 hr at 25° C. in 100 µl volume of TBS containing 0.1% NP-40 and 1 mM MnCl$_2$, as described by Koivunen et al. (1993), supra. After repeated washing, the bound radioactivity was quantitated with a gamma counter.

EXAMPLE IX

CELL ATTACHMENT ASSAY

This example demonstrates the integrin-binding specificity of the peptides of the invention.

Cell lines expressing different integrins were used to examine peptide inhibition of integrin function. A human melanoma cell line, C8161, a fibroblast cell line, WI-38, and an osteosarcoma cell line, MG-63 (described by Seftor et al., *Canc. Res.* 53:3411-3415 (1993); Vogel et al., *J. Biol. Chem.* 265:5934-5937 (1990); and Pytela et al. (1985), supra, respectively, each of which is incorporated herein by reference) attach to fibronectin through $\alpha_5\beta_1$ integrin, as does B2/$\alpha$27, a CHO cell line transfected with human $\alpha_5$.

B2/C1, the control parental CHO line (Bauer et al., *J. Cell. Biol.* 116:477-487 (1992), which is incorporated herein by reference), attaches via $\alpha_v\beta_5$. CHO cells C11 and NIH 3T3 cells express the endogenous Chinese hamster and mouse $\alpha_5\beta_1$ integrins, respectively. The human melanoma cells, A375-M, attach to fibronectin through both $\alpha_5\beta_1$ and $\alpha_4\beta_1$ integrins (Mould et al., *J. Biol. Chem.* 265:4020-4024 (1990), which is incorporated herein by reference). CHO cell line B2/v7 express the $\alpha_v\beta_1$ integrin (Zhang et al., *J. Cell. Biol.* 122:235-242 (1993), which is incorporated herein by reference). The vitronectin-binding integrins $\alpha_v\beta_1$ and $\alpha_v\beta_3$ were assayed using the cell line HT-29 and IMR-90, respectively (Koivunen et al. (1993), supra).

Cell lines expressing fibronectin-binding integrins were used to determine peptide activities against these integrins in the cell attachment assay described by Ruoslahti et al., *Meth. Enzymol.* 144:803-831 (1982), which is incorporated herein by reference. Human plasma fibronectin was iodinated as described by Morla and Ruoslahti, *J. Cell Biol.* 118:421-429 (1992), which is incorporated herein by reference. Vitronectin was obtained from Telios Pharmaceuticals (San Diego, Calif.). In different experiments, microtiter wells were coated either with various concentrations of fibronectin or vitronectin or with a concentration that resulted in 50-70% maximum attachment for each cell type (B2/$\alpha$27, 2 µg/ml; B2/v7, 4 µg/ml; HT29, 8 µg/ml; IMR90, 1 µg/ml). Peptide was coated on plastic by incubating at 37° C. for 2 hr in phosphate buffered saline containing 0.25% glutaraldehyde to crosslink the peptide. Free binding sites on the plastic were blocked using BSA. Approximately 1×10$^5$ cells per well were allowed to attach for 1 hr in the presence or absence of competing peptides. Bound cells were quantitated by staining with 0.1% amido black.

EXAMPLE III

DETERMINATION OF RELATIVE BINDINGS AFFINITIES OF PEPTIDES

The cyclic peptides GACRRETAWACGA [SEQ ID NO:3] (*CRRETAWAC*) [SEQ ID NO:6] and GA*CRGDC*LGA [SEQ ID NO:2] (*CRGDC*) [SEQ ID NO:8] were synthesized using an Applied Biosystems Model 430A synthesizer (Foster City, Calif.) and purified by reverse-phase HPLC. Aliquots of the cyclic peptides were linearized by reduction and alkylation. Briefly, 5 mg of peptide were incubated for 1 hr at 37° C. in 0.1M Tris buffer (pH 8) containing 8M urea and 100× molar excess of dithiothreitol. A 200× molar excess of iodoacetamide was added and the incubation was continued for 30 min in the dark. The peptide was dialyzed extensively against water using a membrane with 500 dalton molecular weight cut off. The recovery of the peptide after dialysis was 43% as determined by UV absorbance.

Relative affinities of the CRRETAWAC [SEQ ID NO:6] and CRGDC [SEQ ID NO:8] peptides were determined by inhibition of binding of peptide-displaying phage to $\alpha_5\beta_1$ integrin. Peptide-displaying phage were constructed as described by Scott and Smith (1990), supra. Microwell plates were coated with various integrins as described by Pytela et al. (1985; 1987), supra.

The binding of CRRETAWAC[SEQ ID NO:6]-containing peptide ligands to $\alpha_5\beta_1$ integrin was performed as follows. RRETAWA[SEQ ID NO:5]-displaying phage were incubated for 1 hr in the presence of various concentrations of the cyclic peptides CRRETAWAC [SEQ ID NO:6] and CRGDC [SEQ ID NO:8] in microtiter wells coated with the $\alpha_5\beta_1$ integrin. Specific binding was quantitated by adding K91kan bacteria directly to the wells and growing the bacteria overnight at room temperature (Smith and Scott, *Meth. Enzymol.* 217:228–257 (1993), which is incorporated herein by reference).

Figure 4:
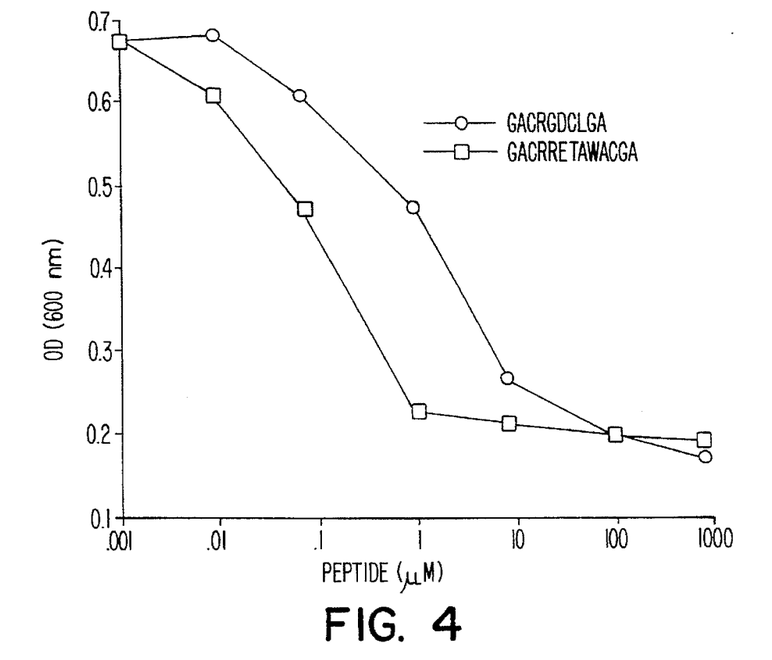
FIG. 4 shows the inhibition of binding of RRETAWA [SEQ ID NO:5]-displaying phage to $\alpha_5\beta_1$ integrin by the cyclic peptides GACRRETAWACGA [SEQ ID NO:3] and GACRGDCLGA [SEQ ID NO:2].

FIG. 4 shows the inhibition of RRETAWA[SEQ ID NO:5]-displaying phage binding to $\alpha_5\beta_1$ integrin by CRGDC [SEQ ID NO:8] and CRRETAWAC [SEQ ID NO:6]. The CRRETAWAC motif inhibited about 10 times more efficiently than the CRGDCL [SEQ ID NO:4] containing peptides. A control peptide GRGESP [SEQ ID NO:12] had no effect (not shown).

Figure 2:
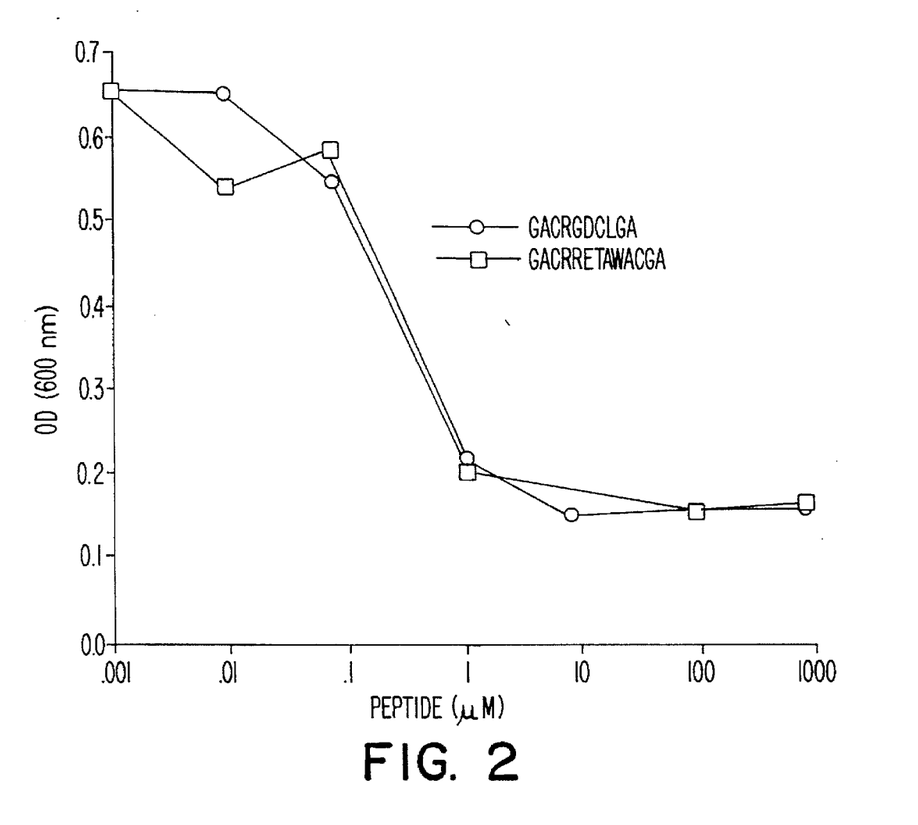
FIG. 2 shows the inhibition of binding of ELRGDGW [SEQ ID NO:1]-displaying phage to $\alpha_5\beta_1$ integrin by synthetic cyclic peptides GACRGDCLGA [SEQ ID NO:2] and GACRRETAWACGA [SEQ ID NO:3].

Additional peptide motifs were tested as follows. ELRGDGW[SEQ ID NO:1]-displaying phage were added together with various concentrations of the cyclic peptides CRRETAWAC [SEQ ID NO:6] and CRGDC [SEQ ID NO:8] into microtiter wells coated with the $\alpha_5\beta_1$ integrin, incubated for 1 hr at room temperature and specific binding wells was quantitated. As shown in FIG. 2, the CRRETAWAC [SEQ ID NO:6] and CRGDC [SEQ ID NO:8] inhibit the binding of ELRGDGW[SEQ ID NO:1]-displaying phage to $\alpha_5\beta_1$ integrin to approximately the same degree of inhibition.

Figure 3:
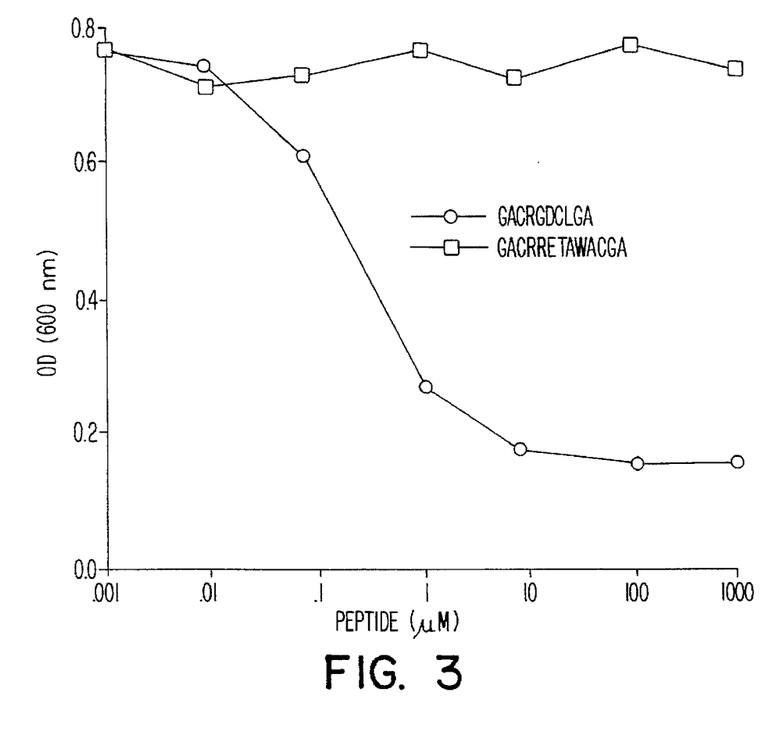
FIG. 3 shows the effect on binding of CRGDCL [SEQ ID NO:4]-displaying phage to $\alpha_v\beta_3$ integrin by the cyclic peptides GACRRETAWACGA [SEQ ID NO:3] and GACRGDCLGA [SEQ ID NO:2].

The ability of CRRETAWAC [SEQ ID NO:6] and CRGDC [SEQ ID NO:8] peptides to inhibit binding of CRGDCL[SEQ ID NO:4]-displaying phage to the microwells coated with $\alpha_v\beta_1$ integrin also was examined. CRGDCL [SEQ ID NO:4]-displaying phage were added to a well and either cyclic GACCRETAWACGA [SEQ ID NO:3] or cyclic GACRGDCLGA [SEQ ID NO:2] was added to compete for binding. Specific binding was quantitated as described above. As shown in FIG. 3, the GACRRETAWACGA [SEQ ID NO:3] peptide was ineffective in inhibiting binding of CRGDCL[SEQ ID NO:4]-displaying phage to $\alpha_v\beta_3$ whereas the GACRGDCLGA [SEQ ID NO:2] peptide completely inhibited binding at concentrations between 10 and 60 µM.

EXAMPLE IV

SPECIFICITY OF RRETAWA FOR $\alpha_5\beta_1$ IN CELL ATTACHMENT AND INHIBITING FIBRONECTIN BINDING The results above indicated that the RRETAWA [SEQ ID NO:5] motif exhibited high relative affinity and specificity for $\alpha_5\beta_1$. To confirm this result, the RRETAWA[SEQ ID NO:5]-containing peptide CRRETAWAC [SEQ ID NO:6] was further tested in additional binding assays and in cell attachment assays. The methods used are identical to those described above.

Initially, CRRETAWAC [SEQ ID NO:6] was examined for its ability to inhibit binding of fibronectin, which is the natural ligand for $\alpha_5\beta_1$. Briefly, $^{125}$I-fibronectin was incubated for 1 hr in the presence of competing peptides in microtiter wells coated with $\alpha_5\beta_1$. Following incubation, the wells were washed and bound radioactivity was determined with a gamma counter. As shown in FIG. 1, the cyclic CRRETAWAC [SEQ ID NO:6] peptide inhibits fibronectin binding equally as well as the cyclic CRGDC [SEQ ID NO:8] peptide. The IC$_{50}$ for both cyclic peptides was observed at about $8\times10^{-9}$M.

Figure 5:
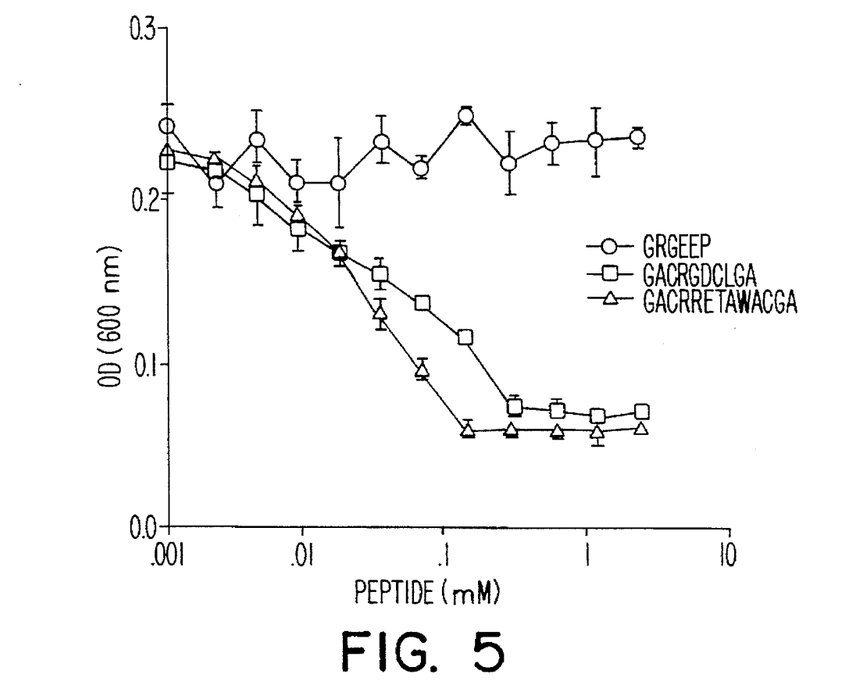
FIG. 5 shows the inhibition of $\alpha_5\beta_1$-mediated cell attachment to fibronectin by synthetic peptides.
Figure 6:
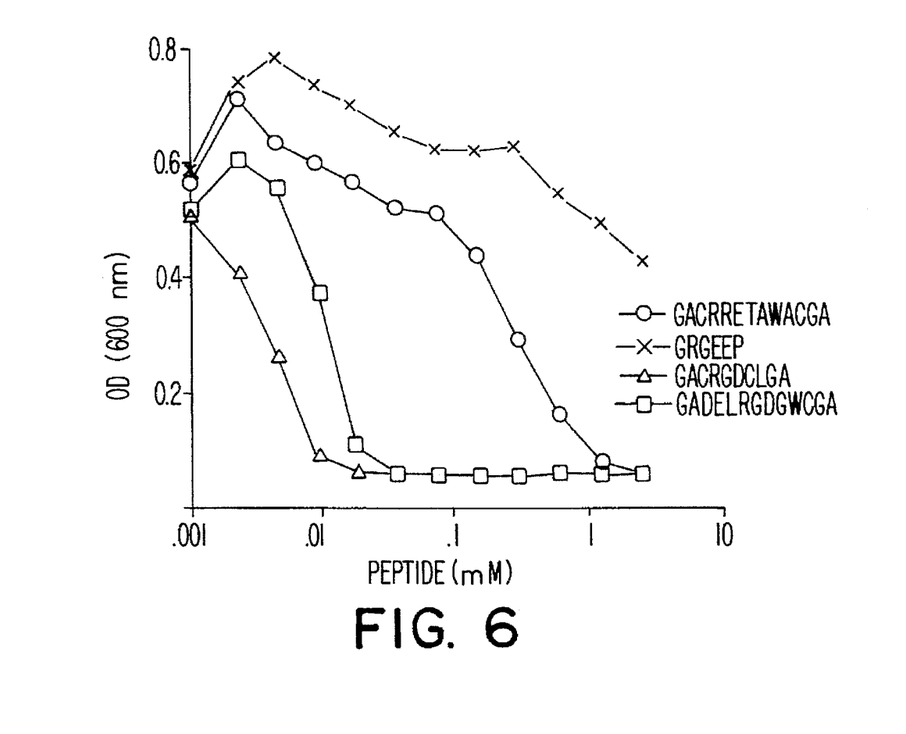
FIG. 6 shows the inhibition of $\alpha_v\beta_1$-mediated cell attachment to fibronectin by synthetic peptides.
Figure 7:
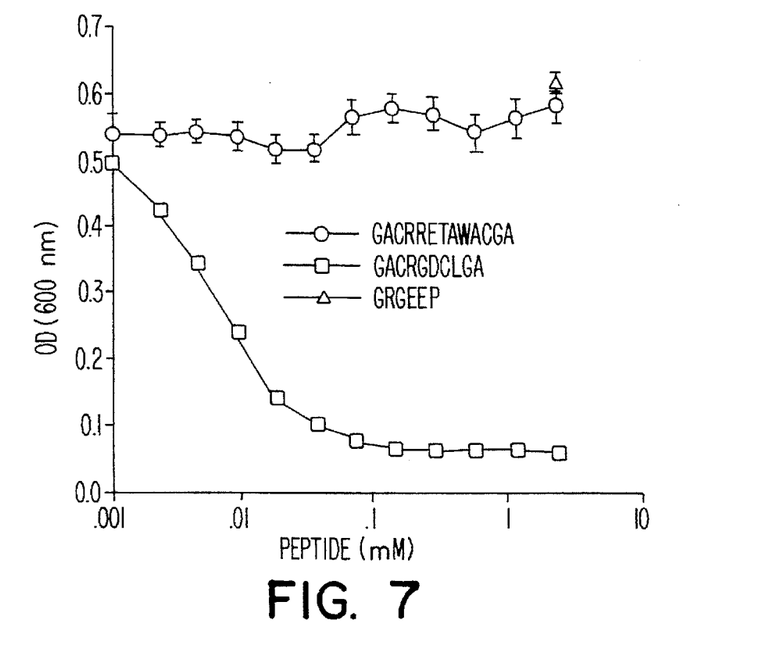
FIG. 7 shows the inhibition of $\alpha_v\beta_5$-mediated cell attachment to vitronectin by synthetic peptides.

Inhibition of cell attachment mediated by either fibronectin- or vitronectin-binding integrins was performed to determine peptide specificity in a biologically relevant system. The assays and cell lines were performed as described above. FIGS. 5 and 6 show the results of cell attachment mediated by the fibronectin binding integrins $\alpha_5\beta_1$ and $\alpha_v\beta_1$. FIG. 7 shows cell attachment mediated by the $\alpha_v\beta_5$ vitronectin binding integrin.

The cell attachment inhibition assays confirm that the RRETAWA [SEQ ID NO:5] peptide is more efficient at inhibiting binding to $\alpha_5\beta_1$ than the cyclic CRGDCL [SEQ ID NO:4] peptide (FIG. 5). The IC$_{50}$ of CRRETAWAC[SEQ ID NO:6]-inhibited $\alpha_5\beta_1$-mediated cell attachment to fibronectin was $3\times10^{-5}$M. The peptide also inhibited cell attachment to a 110 kilodalton fragment of fibronectin that contains the cell attachment domain (not shown). Reduction and alkylation of the disulfide bond reduced the activity of the peptide about 50× (not shown). The control peptide GRGESP [SEQ ID NO:12] had no effect on binding (FIG. 5).

The results in FIG. 5 were obtained using B2/$\alpha$27 cells, which express the human $\alpha_5$ subunit expressed from a transfected cDNA. However, similar results were obtained using the C8161, MG-63 and WI-38 human cell lines, which all express $\alpha_5\beta_1$. The attachment of A375-M cells was only partially inhibited by CRRETAWAC [SEQ ID NO:6], possibly because this cell line expresses other fibronectin-binding integrins such as $\alpha_4\beta_1$ (Mould et al. (1990), supra). However, CRRETAWAC [SEQ ID NO:6] could not block attachment of CHO C11 cells or mouse NIH 3T3 cells to fibronectin (not shown), indicating the peptide may be species-specific.

When tested against another fibronectin binding integrin, $\alpha_v\beta_1$, however, the RRETAWA [SEQ ID NO:5] peptide was greater than 100× less active than the cyclic RGD peptide and about 40× less active than another integrin binding peptide studied, CELRGDGWC [SEQ ID NO:9] (FIG. 6). Finally, when tested against $\alpha_v\beta_5$ cell attachment to vitronectin, the RRETAWA [SEQ ID NO:5] containing peptide was essentially devoid of activity at all concentrations tested (FIG. 7). Combined with the binding data discussed above, these results demonstrate that the GACRRETAWACGA [SEQ ID NO:3] peptide exhibits high affinity and specificity for the $\alpha_5\beta_1$ integrin, but not for other RGD binding integrins.

In addition to the inhibition of cell attachment to natural ligands, attachment and inhibition assays were performed using the GACRRETAWACGA [SEQ ID NO:3] peptide as substrate. The microtiter well were coated with GACRRETAWACGA [SEQ ID NO:3] using glutaraldehyde as described above. Briefly, peptide was coated on plastic by incubating at 37° C. for 2 hr in phosphate buffered saline containing 0.25% glutaraldehyde to crosslink the peptide and free binding sites on the plastic were blocked using BSA. The wells were then saturated with BSA followed by the addition of 50,000 B2/$\alpha$27 or B2/Cl cells in the presence or absence of the indicated inhibitor. The B2/$\alpha$27 cells express $\alpha_5\beta_1$ whereas the B2/Cl do not. Bound cells were quantitated by staining with 0.1% amido black.

Figure 8:
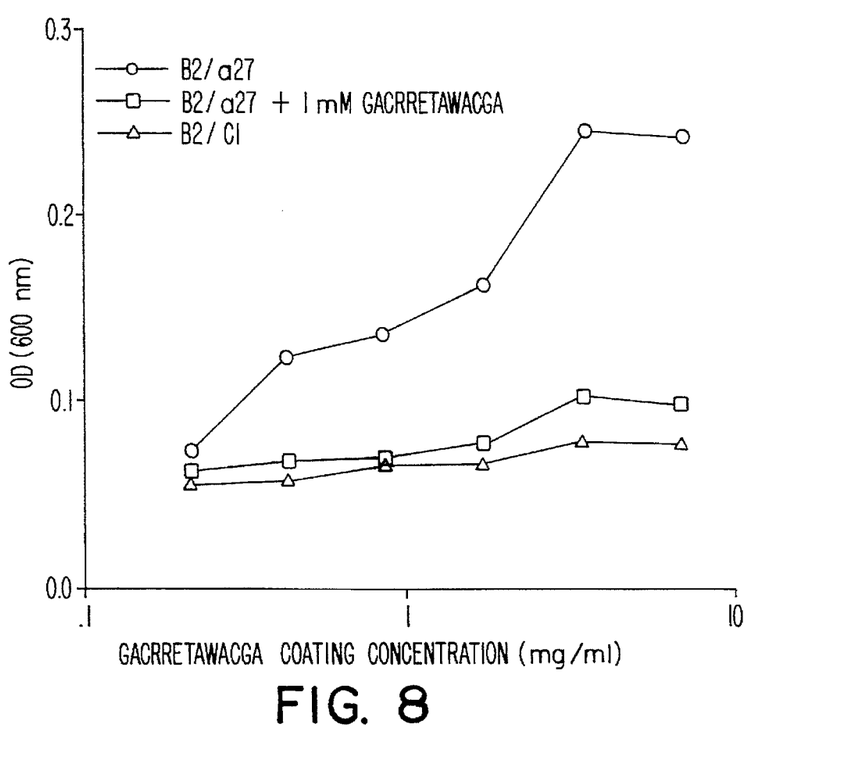
FIG. 8 shows the binding of $\alpha_5\beta_1$-expressing cells and $\alpha_v\beta_5$-expressing cells to the GACRRETAWACGA peptide.

As shown in FIG. 8, the RRETAWA[SEQ ID NO:5]-containing peptide specifically promoted $\alpha_5\beta_1$-mediated adhesion (compare the B2/$\alpha$27 attachment with the B2/Cl). This attachment was inhibited by the RRETAWA[SEQ ID NO:5]-containing peptide (1mM) as well as by CRGDC [SEQ ID NO:8] (1 mM) and by EDTA (10 mM). The $\alpha_v\beta_1$-expressing B2/v7 cells also bound to the peptide, however, a peptide coating concentration of 1 mg/ml was required to produce significant attachment (not shown). Cell lines that do not express these integrins or express a non-human $\alpha_5\beta_1$ integrin did not attach to immobilized CRRETAWAC [SEQ ID NO:6] (not shown).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( x i ) SEQUENCE DESCRIPTION: SEQ ID NO:1:

```
Glu  Leu  Arg  Gly  Asp  Gly  Trp
 1              5
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( x i ) SEQUENCE DESCRIPTION: SEQ ID NO:2:

```
Gly  Ala  Cys  Arg  Gly  Asp  Cys  Leu  Gly  Ala
 1              5                        10
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( x i ) SEQUENCE DESCRIPTION: SEQ ID NO:3:

```
Gly  Ala  Cys  Arg  Arg  Glu  Thr  Ala  Trp  Ala  Cys  Gly  Ala
 1              5                        10
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( x i ) SEQUENCE DESCRIPTION: SEQ ID NO:4:

```
Cys  Arg  Gly  Asp  Cys  Leu
 1              5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( x i ) SEQUENCE DESCRIPTION: SEQ ID NO:5:

```
Arg  Arg  Glu  Thr  Ala  Trp  Ala
 1              5
```

( 2 ) INFORMATION FOR SEQ ID NO:6:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( x i ) SEQUENCE DESCRIPTION: SEQ ID NO:6:

```
Cys  Arg  Arg  Glu  Thr  Ala  Trp  Ala  Cys
1                   5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( x i ) SEQUENCE DESCRIPTION: SEQ ID NO:7:

```
Gly  Arg  Gly  Asp  Ser  Pro
1                   5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( x i ) SEQUENCE DESCRIPTION: SEQ ID NO:8:

```
Cys  Arg  Gly  Asp  Cys
1                   5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( x i ) SEQUENCE DESCRIPTION: SEQ ID NO:9:

```
Cys  Glu  Leu  Arg  Gly  Asp  Gly  Trp  Cys
1                   5
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i x ) FEATURE:
        ( A ) NAME/KEY: Peptide
        ( B ) LOCATION: 1
        ( D ) OTHER INFORMATION: /note= "Xaa = an amino acid capable
            of forming a disulfide bond."

( i x ) FEATURE:
        ( A ) NAME/KEY: Peptide
        ( B ) LOCATION: 9
        ( D ) OTHER INFORMATION: /note= "Xaa = an amino acid capable
            of forming a disulfide bond."

( x i ) SEQUENCE DESCRIPTION: SEQ ID NO:10:

```
Xaa  Arg  Arg  Glu  Thr  Ala  Trp  Ala  Xaa
1                   5
```

-continued (2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear     (ix) FEATURE:
        (A) NAME/KEY: Peptide
        (B) LOCATION: 3
        (D) OTHER INFORMATION: /note= "Xaa = an amino acid capable
            of forming a disulfide bond."

(ix) FEATURE:
        (A) NAME/KEY: Peptide
        (B) LOCATION: 11
        (D) OTHER INFORMATION: /note= "Xaa = an amino acid capable
            of forming a disulfide bond."

(xi) SEQUENCE DESCRIPTION: SEQ ID NO:11:

Gly Ala Xaa Arg Arg Glu Thr Ala Trp Ala Xaa Gly Ala
    1             5                     10

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear     (xi) SEQUENCE DESCRIPTION: SEQ ID NO:12:

Gly Arg Gly Glu Ser Pro
    1             5

Although the present invention has been described in detail with reference to examples above, it is understood that various modifications can be made without departing from the spirit of the invention. Accordingly, the invention is limited only by the following claims.

We claim:
1. A peptide whose amino acid sequence is GACRRETAWACGA [SEQ ID NO:3].
2. A peptide whose amino acid sequence is CRRETAWAC [SEQ ID NO:6].

* * * * *

UNITED STATES PATENT AND TRADEMARK OFFICE
CERTIFICATE OF CORRECTION

PATENT NO. : 5,627,263
DATED : May 6, 1997
INVENTOR(S) : Ruoslahti et al.

It is certified that error appears in the above-identified patent and that said Letters Patent is hereby corrected as shown below:

Column 1,
Line 4, please delete "CA42507" and replace therefor with -- CA45207 --.
Line 42, please delete "$\alpha_5\beta_3$" and replace therefor with -- $\alpha_5\beta_1$ --.

Column 4,
Line 30, please delete "A used" and replace therefor with -- As used --.

Column 10,
Line 44, please delete "well" and replace therefor with -- wells --.

Signed and Sealed this

Sixth Day of November, 2001

*Attest:*

NICHOLAS P. GODICI
*Attesting Officer*    Acting Director of the United States Patent and Trademark Office